United States Patent [19]

Newton

[11] 4,125,554
[45] Nov. 14, 1978

[54] IODINATED THIOLCARBONATES AND METHOD FOR USE AS RADIOGRAPHIC CONTRAST AGENTS

[75] Inventor: Barry N. Newton, Lafayette, Ind.
[73] Assignee: Alcon Laboratories, Inc., Fort Worth, Tex.
[21] Appl. No.: 836,208
[22] Filed: Sep. 23, 1977

Related U.S. Application Data

[60] Continuation-in-part of Ser. No. 766,062, Feb. 7, 1977, which is a division of Ser. No. 679,393, Apr. 22, 1976, Pat. No. 4,022,814, which is a continuation-in-part of Ser. No. 501,169, Aug. 28, 1974, abandoned.

[51] Int. Cl.² .................... C07C 153/11; A61K 29/02
[52] U.S. Cl. ..................................... 260/455 B; 424/5; 260/609 D
[58] Field of Search ................................... 260/455 B

[56] References Cited
FOREIGN PATENT DOCUMENTS
577,805  12/1956  Italy ..................................... 260/455 B Primary Examiner—Lewis Gotts
Assistant Examiner—Robert C. Whittenbaugh
Attorney, Agent, or Firm—Woodard, Weikart, Emhardt & Naughton

[57] ABSTRACT

Iodinated thiolcarbonates and a method for using the same as radiographic contrast agents in connection with such X-ray techniques as myleography, lymphography, hysterosalpingography, bronchography and sialography. The general formula of such iodonated thiolcarbonate compounds may be characterized as

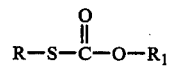

wherein R represents an iodinated phenyl linked to the sulfur through a lower alkylene group consisting of a straight or branched chain having from 1 to 5 carbon atoms and $R_1$ is a lower alkyl group consisting of a straight or branched chain having from 1 to 10 carbon atoms.

18 Claims, No Drawings

IODINATED THIOLCARBONATES AND METHOD FOR USE AS RADIOGRAPHIC CONTRAST AGENTS

BACKGROUND OF THE INVENTION

History of the Invention: This application is a continuation-in-part of a co-pending U.S. patent application, Ser. No. 766,062, filed Feb. 7, 1977 and entitled "Method for Providing a Radiopaque for Radiography Purposes." U.S. patent application, Ser. No. 766,062 is a division of U.S. patent application, Ser. No. 679, 393, filed Apr. 22, 1976 and entitled "Iodine Containing Organic Carbonates for Use as Radiographic Agents," which has since issued as U.S. Pat. No. 4,022,814. U.S. patent application, Ser. No. 679,393 was, in turn, a continuation-in-part of now-abandoned U.S. patent application, Ser. No. 501,169, filed Aug. 28, 1974 and entitled "Iodine Containing Organic Carbonates for Use as Radiographic Agents."

Field of the Invention: This invention relates to contrast media employed in connection with various radiographic techniques, and more particularly, to the preparation and use of iodinated thiolcarbonates as such contrast media for radiographic purposes.

Description of the Prior Art: X-ray visualization techniques for examining various body cavities have been performed for many years, a common example being myleography which involves the study of the subarrachnoide (hereinafter referred to as SA) space from the sacral region through the cervical area in the back. In such applications, three basic classes of contrast agents have been employed: (1) gas; (2) water soluble compounds; and (3) oily, water insoluble compounds.

Gas myleography is the least acceptable technique, requiring the injection of either air or carbon dioxide into the SA space thereby providing a negative contrast. The X-ray interpretation of such an examination is difficult and there is a high incidence of patient headaches. As a result, gas myleography is infrequently used.

Water soluble compounds providing a positive contrast for myleography and other X-ray applications have been used extensively for more than thirty years in Europe. Iodomethane sulfonate was the compound of choice for about three decades, but the incidents of patient reaction, including convulsions and adhesive arachnoiditis, have resulted in its disuse. Other ionic water soluble salts have been used from time to time but the number of side effects has resulted in their not being widely accepted. A dimeric compound is available in the United States, but because of its toxicity it is recommended only for use in the lumbar, sacral region. Nonionic water soluble contrast agents, or "radiopaques" as they are often called, have been prepared by attaching a hydrophilic sugar group to a triiodinated moiety, the first being proposed by J. Hebky, F. First, J. Polack and M. Karasek, Collection Czech. Chem. Commun., 35, 867 (1970). More recently, a nonionic water soluble compound called Metrizamide has been developed and appears to be the least toxic water soluble myleographic media available at the present time. However, reports have surfaced of both moderate to severe adverse patient reactions following Metrizamide myleography and even some seizures have been reported. S. F. Sackett, C. M. Strother, C. E. Quaglieri, M. J. Javid, A. B. Levin, and T. A. Duff, Radiol. 123, 779 (1977).

Oily, water insoluble compounds, on the other hand, have dominated the U.S. market since the early 1940's with ethyl iodophenylundecylate, marketed in the U.S. under the PANTOPAQUE trademark registered to Eastman Kodak Co., Rochester, N.Y., being the most preferred contrast agent. A low incidence of patient side effects has been experienced during this period using the PANTOPAQUE compound. However, as with many of the prior art compounds, PANTOPAQUE is only slowly absorbed and eliminated by the body process and therefore must be withdrawn from the body cavity by a siphonage technique at the conclusion of the examination. Few other new oily contrast materials have been reported in recent years; and of those reported, none exhibit the beneficial qualities of the PANTOPAQUE product.

In general, the ideal radiopaque would be an inert material of relatively high radiographic density in order to provide a good contrast media for the given X-ray application. It would exhibit low viscosity in order to be readily injectable into the body cavity through any conventional variety of relatively small syringe. Once injected, it would form a glob, or "bolus" as it is commonly called, of sufficient thickness to provide a good background for the X-ray; and this bolus would flow freely within the cavity in order to allow adequate X-ray visualization of the entire area. It would also exhibit a high Approximate Lethal Dose, hereinafter referred to as ALD, i.e., possess low toxicity. Finally, it would exhibit rapid elimination by the normal body processes, i.e., in the range of about two weeks or less, in order to avoid any need for surgical withdrawal at the conclusion of examination.

The prior art radiopaques already discussed fall far short of the ideals set forth in the previous paragraph. Radiographic densities are often unsatisfactorily low and toxicity and viscosity readings along with the incidence of patient side effects are dangerously high. In addition, such prior art compounds require substantially long periods for natural elimination by the body processes, many of such periods being so prolonged that it is necessary to surgically remove the injected compound at the completion of the examination.

A major advance in the area of radiographic agents occurred with applicant's discovery of iodine-containing organic carbonates and their beneficial qualities when used as X-ray contrast media. As disclosed in U.S. Pat. No. 4,022,814 issued to Barry N. Newton, these new compounds provide improved radiographic media which are readily eliminated by the body functions in a reasonable length of time, possess relatively low toxicity, are readily administered, and demonstrate minimal irritating and other undesirable side effects. The method of using such new materials is disclosed in both the above issued patent and a pending divisional application thereof, U.S. patent application, Ser. No. 766,062, of which this application is a continuation-in-part.

Nevertheless, even with applicant's prior discovery of iodine containing carbonates, the search continues for the ideal radiographic agent, as above described. In this regard, low toxicity and viscosity and rapid elimination remain the major parameters upon which the search is based.

SUMMARY OF THE INVENTION

One embodiment of the present invention comprises a compound of the formula

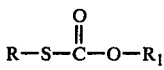

wherein R is an iodinated phenyl linked to the sulfur through a lower alkylene group consisting of a straight or branched chain having from 1 to 5 carbon atoms and $R_1$ is a lower alkyl group consisting of a straight or branched chain having from 1 to 10 carbon atoms.

It has been found that such iodinated thiolcarbonate compounds, characterized by the above formula, exhibit valuable properties when used as radiographic contrast media and have great potential for use in connection with such current X-ray applications as myleography, lymphography, hysterosalpingography, bronchography and sialography. Such iodinated thiolcarbonates constitute a significant advancement over established prior art radiopaque materials and certain of such thiolcarbonates exhibit markedly improved properties over applicant's own prior discovered iodinated organic carbonate compounds, particularly in the areas of toxicity and rate of elimination by the body processes. In addition, applicant is unaware of any prior development or preparation of iodinated thiolcarbonates in accordance with this one embodiment of the present invention.

A second embodiment of the present invention comprises a process for visualizing an inner body cavity in an individual comprising the steps of selecting an iodinated thiolcarbonate compound which is eliminated by the normal body processes, injecting an amount of the compound into a body cavity, and X-raying the injected cavity.

In one mode of practicing this embodiment, the selecting of an iodinated thiolcarbonate is of a compound of the formula

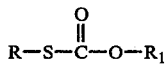

wherein R and $R_1$ are as defined above.

One object of the present invention is to provide new and improved radiographic contrast media which exhibit low viscosity and thus are easily administered, possess low toxicity, minimize irritation and other undesirable side effects, and are readily eliminated by the normal body processes in a reasonable length of time.

Another object of the present invention is to provide new and improved radiographic contrast media suitable for use with such established X-ray applications as myleography, lymphography, hysterosalpingography, bronchography and sialography.

Another object of the present invention is to provide new and improved radiographic contrast media which are readily synthesized and exhibit both stable and nontoxic properties.

Still another object of the present invention is to provide compounds that were previously unknown and which are useful as radiographic materials.

Related objects and advantages of the present invention will be apparent from the following description.

DESCRIPTION OF THE PREFERRED EMBODIMENT

In accordance with one embodiment of the present invention, compounds have been discovered and prepared having the general formula

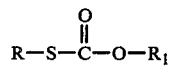

wherein R is an iodinated phenyl linked to the sulfur through a lower alkylene group consisting of a straight or branched chain having from 1 to 5 carbon atoms and $R_1$ is a lower alkyl group consisting of a straight or branched chain having from 1 to 10 carbon atoms. More specifically, the R radical may be depicted by the formula

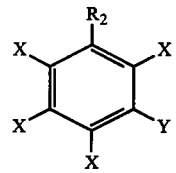

wherein $R_2$ is a lower alkylene group consisting of a straight or branched chain having from 1 to 5 carbon atoms, X is selected from the group consisting of hydrogen and iodine, and Y is selected from the group consisting of hydrogen, iodine and amine. An additional limitation on the compounds is that Y must be an iodine atom whenever X is selected to be hydrogen in order to retain the iodinated state of the thiolcarbonate. Otherwise, no additional limitations of structure need be placed on the compounds of the present invention.

Certain of these iodinated thiolcarbonates, as they are properly called, have been found to exhibit unexpected and valuable properties when used as radiopaques, or radiographic contrast media, in connection with such established X-ray applications as myleography, lymphography, hysterosalpingography, bronchography and sialography. Such iodinated thiolcarbonates, as set forth below, are easily administered, provide sufficiently dense backgrounds for the X-ray applications and are readily absorbed and eliminated by the normal body processes thereby eliminating the need for surgical siphonage or any other method of physically removing the compounds from the body cavity after the examination is completed.

In addition, these certain iodinated thiolcarbonates combine relatively high ALD's, i.e., low toxicities, with relatively low viscosities. Such a combination of traits is a major improvement over established prior art radiographic media and a marked advance over the iodinated organic carbonates which form the subject matter of applicant's prior patent, U.S. Pat. No. 4,022,814, which is expressly incorporated herein by reference as to all relevant portions thereof. Preliminary experimentation with these iodinated carbonates had suggested that such combined low toxicities and viscosities are virtually unobtainable because of an inverse relationship which exists between a given compound's ALD and its viscosity. Such experimentation had further suggested that this inverse relationship is keyed to the number of carbon atoms in the alkyl portion of the compound, with an increase in the carbon content resulting in a corresponding increase in ALD, i.e., lower toxicity, and an increase in viscosity.

Although iodinated thiolcarbonates according to this embodiment of the present invention may contain as many as 5 iodine atoms substituted in the aromatic ring, as suggested by the above formulation, the preferred form of such compounds prepared in accordance with the present invention includes only a single iodine atom substituted in the para position on the ring. In this regard, the following configurations depict several compounds prepared in accordance with the present invention.

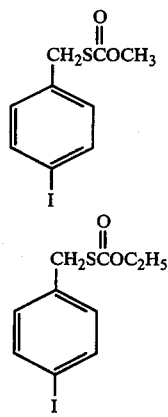

As for other examples of compounds which may be prepared in accordance with the present invention, applicant refers to configurations (a) through (u) in U.S. Pat. No. 4,022,814, which has been heretofore incorporated herein by reference. Such configuration depict various iodinated carbonate compounds according to applicant's previous invention. However, structural transformation of such carbonate configurations to depict the various corresponding thiolcarbonate configurations according to the present invention graphically requires only the substitution of a sulfur atom for the lead oxygen in the carbonate radical.

Toxicity data for applicant's several iodinated thiolcarbonate compounds accompanies the specific examples set forth herein below. Such ALD readings were obtained by injecting 6 albino mice intraperitoneally with graduated doses of each compound, each dose being 50% higher than the preceding. Using this technique, all doses up to a certain level resulted in survival of the animals, while above this level all doses were lethal. Such procedure maps the method of Deichmann and LeBlanc, as described in *W. B. Deichmann and T. J. LeBlanc, J. Ind. Hyg. Toxicol*, 25, 415 (1943); and similar tests conducted using such procedures have been found to agree with their $LD_{50}$ readings within the limits of approximately ±30%.

Synthesis of the iodinated thiolcarbonate compounds of the present invention was accomplished by using the following illustrated procedure, with S-(p-iodobenzyl)-methyl thiolcarbonate being used as a sample compound.

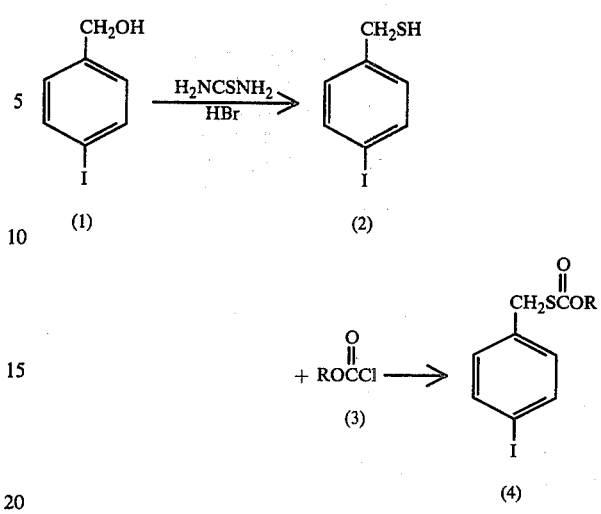

Specifically, the p-iodobenzyl thiol was prepared by reacting the iodinated alcohol (1) with an amount of thiourea and a solution of hydrogen bromide. The combination was heated and stirred and allowed to react for about 16 hours. After refluring in 10% sodium hydroxide, the reaction mixture was acidified (HCl) and the product extracted into ether. After drying the product was vacuum distilled to give the colorless p-iodobenzyl thiol oil (2). This oil was then converted to the appropriate iodinated thiolcarbonate by adding the appropriate alkyl chloroformate (3), here methyl chloroformate, in a suitable solvent, e.g., chloroform, to a solution of the p-iodobenzyl thiol in pyridine and chloroform at 0° C. After refluxing for 30 minutes the product was extracted into chloroform, washed with dilute HCl, dried, and filtered. Vacuum distillation then yields the iodinated thiolcarbonate product (4), in this case S-(p-iodobenzyl) methyl thiolcarbonate.

Although the situation did not arise with the preparation of the various iodinated thiolcarbonates specifically set forth below, the preparation of the initial p-iodobenzyl alcohol (1) may readily be accomplished by following the procedure set forth in column 8 of applicant's prior patent, U.S. Pat. No. 4,022,814. In addition, such prior patent discloses an appropriate procedure to follow should the needed alkyl chloroformate (3) not be readily accessible.

A second embodiment of the present invention comprises a method for visualizing an inner body cavity in a person including the first step of selecting an iodinated thiolcarbonate compound prepared in accordance with applicant's invention and exhibiting the trait of being eliminated by the normal body processes as further discussed hereinbelow. An amount of the selected iodinated thiolcarbonate is injected into the subject body cavity and an X-ray study is then made of the injected area. In this regard, "an X-ray study" means that one or more X-rays are taken of the injected cavity often from different angles in order to get a more complete picture of the condition of the injected area. In addition, the X-rays are often taken over an extended period of time as the bolus of iodinated thiolcarbonate moves and flows through the cavity thereby providing a complete visualization of the subject cavity. This "extended period" can be from about 30 minutes to about one day or longer depending, of course, upon the initial size of the injected bolus, the specific compound used and its viscosity, and the relative size of the subject cavity.

When the X-ray study is complete, the visualization process is ended, with the final step being merely to allow the injected iodinated thiolcarbonate to be absorbed and eliminated by the normal body processes. In this regard, the process and iodinated thiolcarbonates of the present invention constitute a significant improvement over established prior art processes and radiopaques and a marked advance over applicant's own iodinated carbonate compounds in that initial tests suggest the rate of degradation for these iodinated thiolcarbonates is significantly increased. Specifically, the tests suggest the iodinated thiolcarbonates may be readily absorbed and eliminated by the normal body processes within a period of less than about 12 weeks, depending, once again, upon the initial size of the injected bolus, the specific compound used and its viscosity, and the relative size and location of the subject cavity. This means that no surgical or other method will be needed to remove the radiopaque from the cavity after examination.

Specific examples are now presented as further illustrations of the present invention and should not be considered in any way as limitations or restraints on the invention as discussed herein and defined in the attached claims. With this one caveat, examples of the preparation of several iodinated thiolcarbonate compounds according to the present invention are as follows. In such examples, all temperatures are given in "°C" and "%" in percent by weight. In addition, toxicity data stated in terms of ALD (ml/Kg) is given for the individual compounds, and except as expressly noted, sample preparation was accomplished using the procedures detailed in Example I(a) and (b).

EXAMPLE I

S-(p-Iodobenzyl)Methyl Thiolcarbonate (a) A solution was prepared by combining 47 g of p-iodobenzyl alcohol, 101 g of hydrobromic acid (48%) and 15 g of thiourea in 100 ml of water. The solution was continuously stirred and heated to 120° and the reaction allowed to proceed for 16 hours. Next, the solution was refluxed with 250 ml of 10% NaOH for 2 hours. The mixture was then acidified with dilute HCl and the product extracted into ether, dried, filtered and concentrated. At that time, the p-iodobenzyl thiol product was vacuum distilled at 88° and 1 mm Hg to give a colorless oil with a refractive index ($n^{25}D$) of 1.6640. An 87% yield of the thiol product was thereby obtained and it registered an ALD of 1.7 ml/Kg. An analysis found (in percent): C, 33.77; H, 2.80; I, 50.70; and S, 12.55. This analysis was in close agreement with the proposed structure calculated for $C_7H_7IS$ of: C, 33.60; H, 2.83; I, 50.75; and S, 12.82.

(b) Methyl chloroformate (15 ml) in chloroform (10 ml) was then added dropwise to a solution of 15 g of the p-iodobenzyl thiol; 10 ml of pyridine and 15 ml of chloroform at 0°. After refluxing for 30 minutes, the resultant product was extracted into chloroform, washed with dilute HCl, dried and filtered. Vacuum distillation at 130° and 0.8 mm Hg gave 13.9 g (79% yield) of S-(p-iodobenzyl) methyl thiolcarbonate with $n^{25}D$ of 1.6154. Similar analysis to that described in (a) above found (in percent): C, 35.13; H, 2.90; I, 41.06; and S, 10.10. This confirmed the product as $C_9H_9IO_2S$, which exhibits a proposed structure of: C, 35.06; H, 2.95; I, 41.20; and S, 10.41. The thiolcarbonate compound exhibited an ALD of 2.6 ml/Kg.

EXAMPLE II

S-(p-Iodobenzyl) Ethyl Thiolcarbonate 15 g of p-iodobenzyl thiol was combined in solution with 15 ml of ethyl chloroformate. After refluxing for 30 minutes, the product was extracted into chloroform, washed with dilute HCl, and then dried and filtered. Vacuum distillation at 120°–122° and 1.3 mm Hg gave an 88% yield of thiolcarbonate product having an ALD of 2.6 ml/Kg and registering a refractive index of $n^{25}D$ = 1.5996. Analysis confirmed the product to be S-(p-iodobenzyl) ethyl thiolcarbonate having a formula of $C_{10}H_{11}IO_2S$.

EXAMPLE III

S-(p-Iodobenzyl)-n-Butyl Thiolcarbonate 12 g of p-iodobenzyl thiol was combined in solution with 10 ml butyl chloroformate. Vacuum distillation at 137° and 0.6 mm Hg gave a 49% yield of product with an ALD of 1.5 ml/Kg and a refractive index of $n^{25}D$ = 1.5785. Analysis confirmed the product to be S-(p-iodobenzyl)-n-butyl thiolcarbonate having a formula of $C_{12}H_{15}IO_2S$.

EXAMPLE IV

S-(p-Iodobenzyl)-n-Hexyl Thiolcarbonate 14.8 g of p-iodobenzyl thiol was combined in solution with 11 ml of n-hexyl chloroformate and the product vacuum distilled at 161° and 0.07 mm Hg. An 80% yield of S-(p-iodobenzyl)-n-hexyl thiolcarbonate was confirmed having a refractive index of $n^{25}D$ = 1.5657, an ALD of 4.5 ml/Kg and a formula of $C_{14}H_{19}IO_2S$.

EXAMPLE V

S-(p-Iodobenzyl)-n-Octyl Thiolcarbonate 15 g of p-iodobenzyl thiol was combined in solution with 12 ml of n-octyl chloroformate and the thiolcarbonate product vacuum distilled at 204° and 1.6 mm Hg. A 50% yield of S-(p-iodobenzyl)-n-octyl thiolcarbonate was confirmed having a refractive index of $n^{25}D$ = 1.5515, an ALD of 15.2 ml/Kg and a formula of $C_{16}H_{23}IO_2S$.

EXAMPLE VI

S-(p-Iodobenzyl)-n-Decyl Thiolcarbonate 16.6 g p-iodobenzyl thiol was combined in solution with 15 g n-decyl chloroformate, prepared from 15 g n-decyl alcohol and phosgene using known procedures as described in column 8 of U.S. Pat. No. 4,022,814, heretofore incorporated herein by reference, and the thiolcarbonate product vacuum distilled at 190° and 0.05 mm Hg. A 50% yield of S-(p-iodobenzyl)-n-decyl thiolcarbonate was confirmed having a refractive index of $n^{25}D$ = 1.5341, an ALD of 22.5 ml/Kg and a formula of $C_{18}H_{27}IO_2S$.

EXAMPLE VII

S-(p-Iodobenzyl)-2-Methylpropyl Thiolcarbonate 14.5 g of p-iodobenzyl thiol was combined with 6 g of 2-methyl propyl chloroformate, prepared as described in column 8 in U.S. Pat. No. 4,022,814, and the product vacuum distilled at 152°–155° and 0.3 mm Hg. A 40% yield of S-(p-iodobenzyl)-2-methylpropyl thiolcarbonate was confirmed having a refractive index of $n^{25}D$ =

EXAMPLE VIII

S-(p-Iodobenzyl)-2-Hexyl Thiolcarbonate 16 g of p-iodobenzyl thiol was combined in solution with 15 g of 2-hexyl chloroformate, prepared as described in column 8 in U.S. Pat. No. 4,022,814; and the product vacuum distilled at 157° and 0.09 mm Hg. A 35% yield of S-(p-iodobenzyl)-2-hexyl thiolcarbonate was confirmed having a refractive index of $n^{25}D = 1.5631$, an ALD of 6.7 ml/Kg and a formula of $C_{14}H_{19}IO_2S$.

EXAMPLE IX

S-(p-Iodobenzyl)-2-Octyl Thiolcarbonate 15 g of p-iodobenzyl thiol was combined in solution with 10 g of 2-octyl chloroformate, prepared as described in column 8 in U.S. Pat. No. 4,022,814, and the product vacuum distilled at 178°–181° and 0.2 mm Hg. A 79% yield of S-(p-iodobenzyl)-2-octyl thiolcarbonate was confirmed having a refractive index of $n^{25}D = 1.5505$, an ALD of 15 ml/Kg and a formula of $C_{16}H_{23}IO_2S$.

EXAMPLE X

S-(p-Iodophenethyl)-n-Butyl Thiolcarbonate (a) 104 g of p-iodophenethyl alcohol was combined in solution with 216 g of hydrobromic acid (48%) and 36 g of thiourea in 100 ml of water and reacted in accordance with the procedure outlined in Example I(a). Vacuum distillation at 91°–95° and 0.2 mm Hg gave a 27% yield of p-iodophenethyl thiol having a refractive index of $n^{25}D = 1.6411$, an ALD of 0.56 ml/Kg and a formula of $C_8H_8IS$.

(b) 9.61 g of p-iodophenethyl thiol was then combined in solution with 8 ml of butyl chloroformate using the procedure in Example I(b) and the product vacuum distilled at 149°–154° and 0.15 mm Hg. A 65% yield of S-(p-iodophenethyl)-n-butyl thiolcarbonate was confirmed having a refractive index of $n^{25}D = 1.5711$, an ALD of 3 ml/Kg and a formula of $C_{13}H_{17}IO_2S$.

EXAMPLE XI

S-(p-Iodophenethyl)-n-Hexyl Thiolcarbonate 10 g of p-iodophenethyl thiol was combined in solution with 8 ml of hexyl chloroformate and the product vacuum distilled at 170° and 0.05 mm Hg. A 67% yield of S-(p-iodophenethyl)-n-hexyl thiolcarbonate was confirmed having a refractive index of $n^{25}D = 1.5579$, an ALD of greater than 15.2 ml/Kg and a formula of $C_{15}H_{21}IO_2S$.

EXAMPLE XII

N-Butyl-S[3-(p-Iodophenyl) Butyl] Thiolcarbonate (a) 70 g of 3-(p-iodophenyl) butanol was combined in solution with 138 g of hydrobromic acid (48%) and 20 g thiourea in 100 ml of water and the thiol product vacuum distilled at 126° and 0.18 mm Hg. A 41% yield of 3-(p-Iodophenyl) butane thiol was confirmed having a refractive index of $n^{25}D = 1.6071$ and nmr, ir and gc readings commensurate with the structure of the desired product.

(b) 15 g of 3-(p-iodophenyl) butane thiol was combined in solution with 10 ml of n-butyl chloroformate and the product vacuum distilled at 160° and 0.05 mm Hg. A 25% yield of n-butyl-S[3-(p-iodophenyl)butyl] thiolcarbonate was confirmed having a refractive index of $n^{25}D = 1.5597$ and an ALD of 4.44 ml/Kg.

EXAMPLE XIII

N-Hexyl-S[3-(p-Iodophenyl) Butyl] Thiolcarbonate 15 g of 3-(p-iodophenyl) butane thiol was combined in solution with 30 ml of n-hexyl chloroformate and the product vacuum distilled at 187°–189° and 0.04 mm Hg. A 44% yield of n-hexyl-S[3-(p-iodophenyl) butyl] thiolcarbonate was confirmed having a refractive index of $n^{25}D = 1.5500$ and an ALD of 15.0 ml/Kg.

EXAMPLE XIV

N-Butyl-S-b [3-(p-Iodophenyl) Propyl] Thiolcarbonate (a) 62 g of 3-(p-iodophenyl) propanol was combined in solution with 161 g of hydrobromic acid (48%) and 23 g of thiourea in 100 ml of water and the thiol product vacuum distilled at 114°–117° and 0.1 mm Hg. A 66% yield of 3-(p-iodophenyl) propane thiol was confirmed having a refractive index of $n^{25}D = 1.6202$.

(b) 16.88 g of 3-(p-iodophenyl) propane thiol was combined in solution with 15 ml of n-butyl chloroformate and the product vacuum distilled at 167°–170° and 0.09 mm Hg. A 47% yield of n-butyl-S[3-(p-iodophenyl) propyl] thiolcarbonate was confirmed having a refractive index of $n^{25}D = 1.5633$ and an ALD of 6.67 ml/Kg.

EXAMPLE XV

N-Hexyl-S[3-(p-iodophenyl) propyl] Thiolcarbonate 15.28 g of 3-(p-iodophenyl) propane thiol was combined in solution with 15 ml of n-hexyl chloroformate and the product vacuum distilled at 186°–190° and 0.05 mm Hg. A 54% yield of n-hexyl-S[3-(p-iodophenyl) propyl] thiolcarbonate was confirmed having a refractive index of $n^{25}D = 1.5524$ and an ALD of 22.5 ml/Kg.

EXAMPLE XVI

N-Butyl-S[p-Iodo Sec Phenethyl] Thiolcarbonate (a) 127 g of p-iodo sec phenethyl alcohol was combined in solution with 255 g of hydrobromic acid (48%) and 48 g of thiourea in 100 ml of water and the thiol product vacuum distilled at 88° and 0.05 mm Hg. A 25% yield of p-iodo sec phenethyl thiol was confirmed having a refractive index of $n^{25}D = 1.6368$.

(b) 12.56 g of p-iodo sec phenethyl thiol was combined in solution with 20 ml of n-butyl chloroformate and the product vacuum distilled at 140° and 0.1 mm Hg. A 42% yield of n-butyl-S[p-iodo sec phenethyl] thiolcarbonate was confirmed having a refractive index of $n^{25}D = 1.5714$ and an ALD of 2.96 ml/Kg.

EXAMPLE XVII

N-Hexyl-S[p-Iodo Sec Phenethyl] Thiolcarbonate 12.95 g of p-iodo sec phenethyl thiol was combined in solution with 25 ml of n-hexyl chloroformate and the product vacuum distilled at 125° and 0.05 mm Hg. A 65% yield of n-hexyl-S[p-iodo sec phenethyl] thiolcarbonate was confirmed having a refractive index of $n^{25}D = 1.5598$ and an ALD of 4.44 ml/Kg.

I claim:

1. A compound of the formula

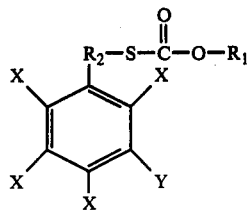

wherein:
(a) $R_2$ is a lower alkylene group consisting of a straight or branched chain having from 1 to 5 carbon atoms;
(b) each X is selected from the group consisting of hydrogen and iodine;
(c) Y is selected from the group consisting of hydrogen, iodine and amine, Y being iodine when all X's are hydrogen; and
(d) $R_1$ is a lower alkyl group consisting of a straight or branched chain having from 1 to 10 carbon atoms.

2. The compound of claim 1 in which the iodinated thiolcarbonate compound is S-(p-iodobenzyl)methyl thiolcarbonate.

3. The compound of claim 1 in which the iodinated thiolcarbonate compound is S-(p-iodobenzyl)ethyl thiolcarbonate.

4. The compound of claim 1 in which the iodinated thiolcarbonate compound is S-(p-iodobenzyl)-n-butyl thiolcarbonate.

5. The compound of claim 1 in which the iodinated thiolcarbonate compound is S-(p-iodobenzyl)-n-hexyl thiolcarbonate.

6. The compound of claim 1 in which the iodinated thiolcarbonate compound is S-(p-iodobenzyl)-n-octyl thiolcarbonate.

7. The compound of claim 1 in which the iodinated thiolcarbonate compound is S-(p-iodobenzyl)-n-decyl thiolcarbonate.

8. The compound of claim 1 in which the iodinated thiolcarbonate compound is S-(p-iodobenzyl)-2-methylpropyl thiolcarbonate.

9. The compound of claim 1 in which the iodinated thiolcarbonate compound is S-(p-iodobenzyl)-2-hexyl thiolcarbonate.

10. The compound of claim 1 in which the iodinated thiolcarbonate compound if S-(p-iodobenzyl)-2-octyl thiolcarbonate.

11. The compound of claim 1 in which the iodinated thiolcarbonate compound is S-(p-iodophenethyl)-n-butyl thiolcarbonate.

12. The compound of claim 1 in which the iodinated thiolcarbonate compound is S-(p-iodophenethyl)-n-hexyl thiolcarbonate.

13. The compound of claim 1 in which the iodinated thiolcarbonate compound is n-butyl-S[3-(p-iodophenyl)butyl] thiolcarbonate.

14. The compound of claim 1 in which the iodinated thiolcarbonate compound is n-hexyl-S[3-(p-iodophenyl)butyl] thiolcarbonate.

15. The compound of claim 1 in which the iodinated thiolcarbonate compound is n-butyl-S[3-(p-iodophenyl)propyl] thiolcarbonate.

16. The compound of claim 1 in which the iodinated thiolcarbonate compound is n-hexyl-S[3-(p-iodophenyl)propyl] thiolcarbonate.

17. The compound of claim 1 in which the iodinated thiolcarbonate compound is n-butyl-S[p-iodo sec phenethyl] thiolcarbonate.

18. The compound in claim 1 containing only from 1 to 3 iodine atoms.

* * * * *